United States Patent [19]

Young

[11] 4,025,394
[45] May 24, 1977

[54] FERMENTATION PROCESSES USING SCRAPED TUBULAR FERMENTOR

[75] Inventor: Murray Moo Young, Waterloo, Canada

[73] Assignee: The University of Waterloo, Waterloo, Canada

[22] Filed: Feb. 17, 1976

[21] Appl. No.: 658,836

[30] Foreign Application Priority Data

May 6, 1975  United Kingdom ............ 19044/75

[52] U.S. Cl. .............................. 195/115; 195/109; 195/142; 195/143
[51] Int. Cl.² ........................................... C12B 1/00
[58] Field of Search ........... 195/109, 115, 142, 143

[56] References Cited

UNITED STATES PATENTS

| 2,530,814 | 11/1950 | Becze et al. | 195/143 |
| 2,952,588 | 9/1960 | Rinderer | 195/143 |
| 3,216,908 | 11/1965 | Kratochnil | 195/143 |

*Primary Examiner*—Raymond N. Jones
*Assistant Examiner*—Robert J. Warden
*Attorney, Agent, or Firm*—Sim & McBurney

[57] ABSTRACT

Fermentation of a substrate by microorganisms capable of utilizing the substrate for growth is improved by conveying a fermentation medium including the substrate and microorganisms through a hollow tube with the assistance of an internal wall-scraper.

29 Claims, 5 Drawing Figures

FERMENTATION PROCESSES USING SCRAPED TUBULAR FERMENTOR

FIELD OF INVENTION

The present invention relates to fermentation processes, more particularly to fermentation processes using a scraped tubular type fermentor.

BACKGROUND TO THE INVENTION

Certain fermentation processes cannot be carried out or, are carried out inefficiently in conventional stirred-tank type fermentors. One class of such fermentation processes is in the continuous production of secondary metabolites, for example, extracellular enzymes, wherein product formation lags behind microbial growth; in this example, a fermentor with plug-flow of fluid through the apparatus would theoretically give a higher productivity than one with mixed-flow.

Another class of such fermentation processes is one in which solid material is continually deposited on the fermentor vessel walls such as from microbial growth, especially of filamentous organisms, polymeric metabolites, or media particulates such as found in the microbial degradation of solid substrates.

Yet another class of such fermentation processes is one in which only mild agitation conditions are required such as for large filamentous growths or media film-surface growths.

In a plug flow of material through a pipe, vessel or the like, individual elements of material do not mix longitudinally in the direction of flow of the material and hence may be considered as isolated from each other. This is in complete contrast to the conventional mixed-flow pattern of a stirred-tank fermentor in which the contents of the process materials are completely mixed throughout the vessel.

SUMMARY OF INVENTION

The present invention provides novel fermentation process and apparatus which enable plug-flow fermentation and/or solids wall-deposit-free fermentation and/or mild-agitation fermentation to occur.

DESCRIPTION OF PREFERRED EMBODIMENTS

Figure 1:
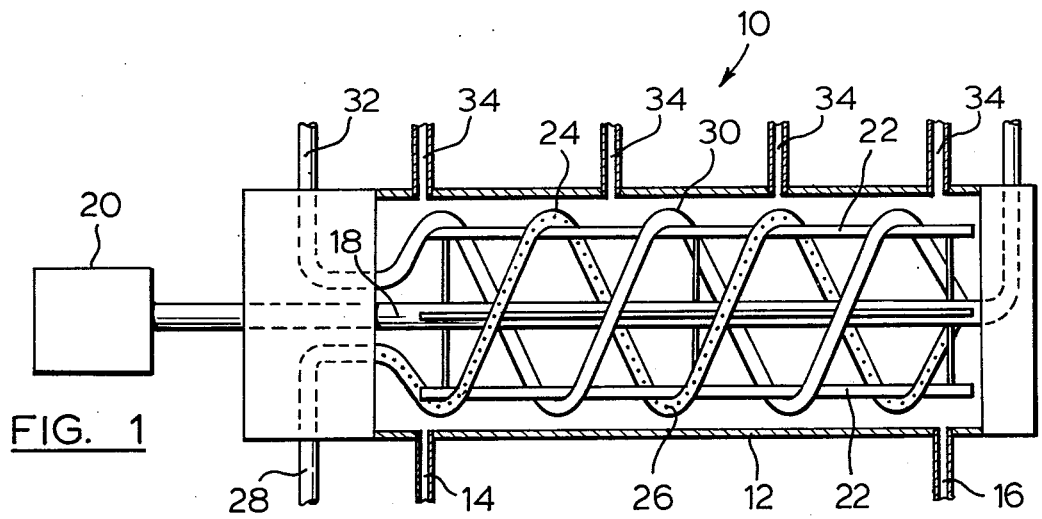
FIG. 1 is a schematic elevational representation of a tubular fermentor used in one embodiment of the invention.

Referring first to the embodiment of FIG. 1, a fermentor 10 includes a tube 12 mounted with its axis extending substantially horizontally and provided with an inlet 14 at one end and an outlet 16 at the other.

Extending internally of the tubular fermentor 10 substantially axially thereof is a shaft 18 mounted for rotation of the tube by a motor 20 of any convenient construction. Spacer rods 22 are mounted to the shaft 14 to extend parallel thereto and arranged in planetary fashion about the shaft 18 for rotation therewith. Any desired number of such spacer rods 22 may be arranged about the shaft 14 to provide mechanical stability.

A first pipe 24 is wound in helical fashion about the spacer rods 22 and is provided with a plurality of perforations 26 along its length to allow the discharge of gas fed to the pipe 24 through pipe 28 within the tube 12. The gas such as nitrogen is used to provide radial mixing of the medium, or if it is air or other gas containing molecular oxygen, to provide radial mixing and aeration of the fermentation medium. The first pipe 24 is arranged so that the radially outer extremity of the helix touches the inner wall of the tube 12.

A second pipe 30 also is wound in helical fashion about the spacer rods 22 in any desired relation to the helix formed by pipe 24. The second pipe 30 communicates with a liquid feed pipe 32 for the passage of liquid through the pipe 30 to act as a thermostatic control medium for the fermentation media in the tube 12.

The second pipe 30 also is arranged so that the radially outer extremity of the helix engages the inner wall of the tube 12.

A plurality of gas vent openings 34 is provided in the tube 12 at any convenient intervals along its length to allow discharge of gases from the tube 12.

In operation, the tube 12 may be maintained partially filled with fermentation media to allow for the accumulation of effluent gas above the media. This effluent gas is vented through the gas vents 34 as required.

The motor 20 rotates the shaft 18 thereby causing rotation of the spacer rods 22 and pipes 24 and 30 within the stationary tube 12.

The helices formed by the pipes 24 and 30 turns via a slip-ring or other suitable device, and, by scraping action, move grown cells or other solids which are deposited onto the inner walls of the tube 12 towards the outlet. These helices also provide partial segregation between medium elements along the stationary tube 12.

The speed of the shaft 18 is coupled to the flow of fermentation medium at slow rates so as not to unduly disturb the axial flow pattern of the medium which thereby moves in plug-like form through the tube 12.

In aerobic fermentations, air bubbles discharged into the liquid medium from the submerged sections of the pipe 24 tend to induce a radial flow pattern which involves no significant axial mixing in the tube 12. Air discharge from the unsubmerged sections of the pipe 24 tend to clean the pipe perforations of possible blockage with solids material, provide media surface-aeration, and flush out effluent gas such as carbon dioxide.

If desired, mixed-flow conditions within the fermentor may be promoted while still maintaining wall-deposit-free operation, by recycling some of the media from the fermentor outlet 16 to its inlet 14 via a suitable connection and/or rotating the shaft 18 at higher speeds.

Figure 2:
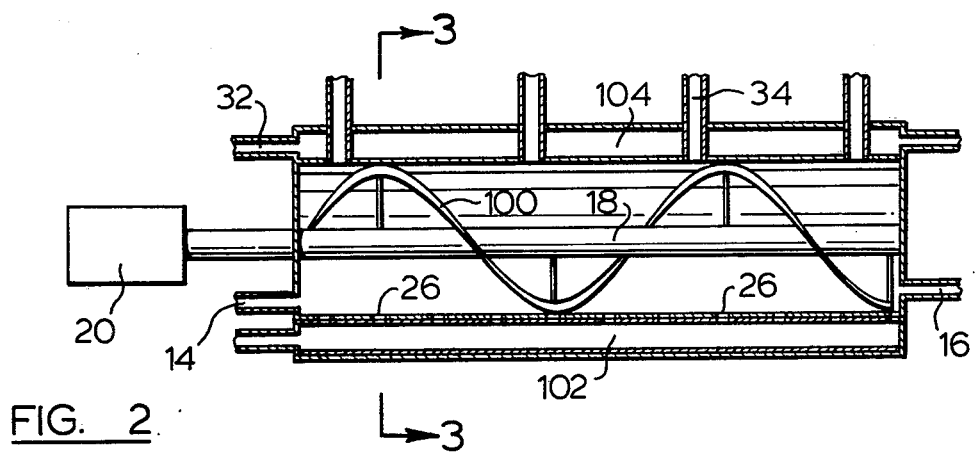
FIG. 2 is a schematic elevational representation of a modified tubular fermentor used in accordance with another embodiment of the invention.
Figure 3:
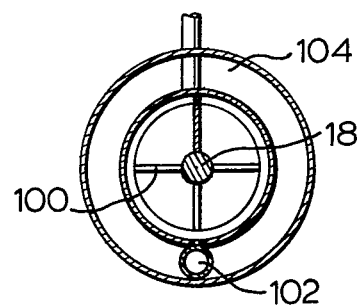
FIG. 3 is a section taken on line 3—3 of FIG. 2.

Referring now to the embodiment of FIGS. 2 and 3, where like reference numerals are used to designate like parts, a helical ribbon, auger or screw 100 is connected to the shaft 18 in place of the coiled pipes 24 and 30 of FIG. 1, thereby providing virtually total segregation between medium elements along the tube 12. Rotation of the shaft 18 causes scraping of the walls of the tube 12 to move solids and liquid in plug-flow through the tube 12 providing a solids wall-deposit-free fermentor.

Also as illustrated in FIGS. 2 and 3, the scraping bubble-generation and heat exchanging facilities provided in the structure of FIG. 1 are separated. Thus, in addition to the screw-type scraper 100, a stationary perforated sparger pipe 102 may be provided coextensive with and along the bottom and exteriorally of the tube 12 in an outer jacket 104 fed with thermostat liquid for heat-exchange purposes. The sparger 102 serves to distribute the air or other suitable gas to the medium radially in the pipe 12. As in FIG. 1, a recycle stream for the medium may be used between any intermediate points along the tube 12.

Figure 4:
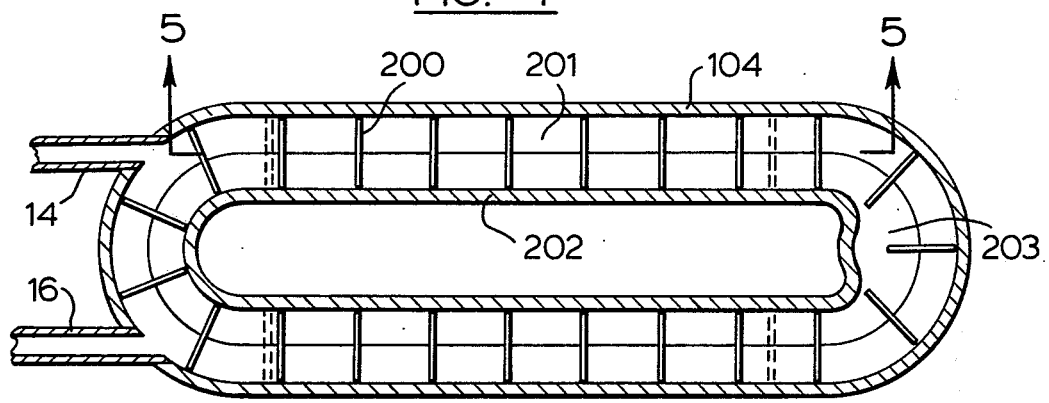
FIG. 4 is a schematic plan representation of another modified tubular fermentor used in accordance with yet another embodiment of the invention.
Figure 5:
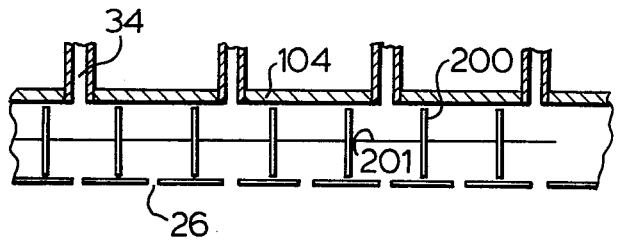
FIG. 5 is a schematic elevational view of the apparatus of FIG. 4.

Referring to the embodiment of FIGS. 4 and 5, where like reference numerals are used to designate like parts, a transport device consisting of a series of disc-plates 200 fixed at suitable intervals along a flexible cable 201 is used in place of the helical ribbon, auger or screw 100 of FIG. 2, to move materials along the tube 202. The continuous double-section tube 202 is used in place of the single-section tube 12 of FIG. 2. The transport device 200 is caused to move along the tube 202 by means of a suitably motorized gear 203. Gas, if required, is provided by a multiplicity of orifices 26 along the bottom of the tube 202, and heat-exchanger facilities are provided by means of an external jacket 104, both facilities being similar to those of FIGS. 2 and 3.

DESCRIPTION OF OTHER EMBODIMENTS

Another important application of the invention is related to the operation of a fermentor as a microbial film-type fermentor in which the medium is in the form of a paste which is moved in plug-flow along the inside walls of the tube as a film on which microorganisms grow. In this case, aeration, if required, is provided by blowing air through the central section of the tube, and the apparatus may be operated in a non-horizontal position.

Another important application of the invention is related to the operation of a fermentor as a tumble-type fermentor in which the medium is in a solid or semi-solid granular form on which microorganisms grow. In this case, aeration for the solid-phase fermentation process is provided by the continuous tumbling of the substrate containing particles as they are lifted by the rotating helical scraper to the top of the tube and allowed to fall under gravity through the air space in the tube to the bottom; simultaneously, the particles may be moved in plug-like flow along the length of the tube to the exit.

If desired, a number of scraped tubular fermentors can be operated in parallel, in series or in a combination of both arrangements.

EXAMPLES

Example I

Using the apparatus of FIG. 1, lipase was formed by a yeast culture of a *Candida lipolytica* strain. Lipase, an extracellular fat-degrading enzyme produced by this culture, is subject to catabolite repression. Test results with the apparatus of FIG. 1 show that the enzyme productivity is significantly higher than that obtained from a conventional stirred-tank fermentor of equivalent volume, the results being reproduced in Table I:

TABLE I

| Dilution Rate ($hr^{-1}$) | Lipase productivity by apparatus of FIG. 1 compared to productivity by conventional stirred-tank fermentor |
|---|---|
| 0.03 | 3.0 |
| 0.05 | 1.9 |
| 0.07 | 1.5 |

EXAMPLE 2

Using the same culture as in Example 1 in the apparatus of FIG. 1, the increase in microbial biomass productivity over that in a conventional stirred-tank fermentor was observed, and the results are reproduced in Table II:

TABLE II

| Dilution Rate ($hr^{-1}$) | Biomass productivity in apparatus of FIG. 1 compared to biomass productivity in conventional stirred-tank fermentor |
|---|---|
| 0.03 | 1.3 |
| 0.05 | 1.2 |
| 0.07 | 1.2 |

EXAMPLE 3

The apparatus of FIG. 2 was used to convert cellulose into biomass using a culture of a fungus, *Trichoderma viride*, without the operational problem of wall-growth and substrate deposits obtained in conventional stirred-tank fermentors. Table III shows typical results for microbial cell-growth, cellulase-enzyme synthesis and cellulose substrate-degradation at suitable dilution rates.

TABLE III

| Fermentor location | Biomass (g/L) | Cellulase (U/ml/min) | Cellulose (g/L) |
|---|---|---|---|
| Inlet | 0 | 0 | 3 |
| Mid-point | 2.2 | 4.8 | 0.8 |
| Outlet | 3.0 | 6.2 | 0 |

SUMMARY

The present invention, therefore, provides a fermentor which is capable of providing a plug flow pattern for a fermentation medium and/or solids wall deposit-free fermentor conditions and/or mild agitation fermentor conditions with consequential benefits and fermentation processes using such a fermentor. Modifications are possible within the scope of the invention.

I claim:

1. A method of fermentation of a substrate by microorganisms capable of utilizing the substrate for growth, which comprises conveying a fermentation medium including said substrate and microorganisms through a hollow uncompartmented tube by scraping means which engage the interior surface of said tube fermenting said substrate by said microorganisms during said conveying of said fermentation medium through said tube, and scraping the internal walls of said tube during said conveying of said fermentation medium through said tube.

2. The method of claim 1, wherein said fermentation is aerobic.

3. The method of claim 2 wherein aeration is provided by blowing air through the tube from the inlet to the outlet end.

4. The method of claim 1, wherein said fermentation is anaerobic.

5. The method of claim 4 wherein said tube is completely full with the medium.

6. The method of claim 1 wherein said tube is partially full with the medium.

7. The method of claim 1 wherein said medium is in the form of a liquid.

8. The method of claim 1 wherein said medium is in the form of a liquid slurry.

9. The method of claim 8 wherein said substrate is in the form of solid particles.

10. The method of claim 9 wherein said substrate is cellulose.

11. The method of claim 10 wherein said microorganism is a mold, Trichoderma viride.

12. The method of claim 1 wherein said medium is in the form of solid particles.

13. The method of claim 1 wherein said medium is in the form of a paste.

14. The method of claim 1 including feeding gas streams into said tube at suitable intervals along the length thereof radially of the tube to achieve radial mixing of said fermentation medium.

15. The method of claim 14 wherein said gas stream contains oxygen to provide aeration in said medium in addition to said radial mixing.

16. The method of claim 1 wherein said scraping is achieved using a helical coil.

17. The method of claim 1 wherein said scraping is achieved using a helical ribbon.

18. The method of claim 1 wherein said scraping is achieved using an auger or screw.

19. The method of claim 1 wherein said scraping is achieved using a series of disc plates mounted substantially at right-angles to the tube walls.

20. The method of claim 1 wherein an extracellular enzyme is produced thereby.

21. The method of claim 20 wherein said extracellular enzyme is a lipase and said microorganism is a Candida lipolytica yeast strain.

22. The method of claim 1 wherein microbial biomass is produced thereby.

23. The method of claim 22 wherein said microbial biomass is a yeast, *Candida lipolytica*.

24. The method of claim 1 including contacting said fermentation medium with heat-exchanger fluid.

25. The method of claim 1 including recycling a portion of the fermentation medium from any section of said tube to any preceding section thereof.

26. The method of claim 1 wherein said tube is a single straight tube.

27. The method of claim 1 wherein said tube is curved.

28. The method of claim 1 wherein said tube is oriented substantially horizontally.

29. The method of claim 1 including maintaining said fermentation medium in a plug flow pattern during said conveying of said fermentation medium through said tube.

* * * * *